United States Patent [19]

Machida

[11] Patent Number: 4,464,777
[45] Date of Patent: Aug. 7, 1984

[54] RADIOGRAPHY APPARATUS
[75] Inventor: Kaoru Machida, Otawara, Japan
[73] Assignee: Tokyo Shibaura Denki Kabushiki Kaisha, Japan
[21] Appl. No.: 311,965
[22] Filed: Oct. 16, 1981
[30] Foreign Application Priority Data Oct. 22, 1980 [JP] Japan ................................. 55-147918
Oct. 25, 1980 [JP] Japan ................................. 55-149894
Oct. 31, 1980 [JP] Japan ................................. 55-153214

[51] Int. Cl.$^3$ ............................................. G03B 41/16
[52] U.S. Cl. ...................................... 378/146; 378/13
[58] Field of Search ........................... 378/146, 13, 20

[56] References Cited
U.S. PATENT DOCUMENTS

4,134,020  1/1979  Zonneveld ............................. 378/13
4,174,481 11/1979  Liebetruth ............................. 378/19

Primary Examiner—Craig E. Church
Attorney, Agent, or Firm—Finnegan, Henderson, Farabow, Garrett & Dunner

[57] ABSTRACT

Disclosed is a radiography apparatus comprising an X-ray tube for radiating X-ray beam in a fan shape, a detector for detecting the X-ray beam coming through a living body at a plurality of angular components of the X-ray beam, and a sampling circuit for sampling an output signal of the detector when the living body moves at a given speed in a direction orthogonal to the plane of the X-ray beam, whereby a radiogram is formed by using the output signal of the sampling circuit. In the radiography apparatus, the distance between the living body and the X-ray tube is variable and is detected by a potentiometer interlocked with the movement of the living body. A pulse signal at a frequency corresponding to an output level of the potentiometer is produced by a pulse frequency modulation circuit, and is supplied as a timing signal to the sampling circuit. Thus, a sampling frequency of the sampling circuit is determined by the distance between the X-ray tube 10 and the living body, so that a radiogram with the same enlargement factor in the X and Y directions is obtained.

14 Claims, 9 Drawing Figures

RADIOGRAPHY APPARATUS

BACKGROUND OF THE INVENTION

The present invention relates to a radiography apparatus for forming a radiogram of a living body.

There has been known, as an apparatus for forming a radiogram in use for a diagnosis of a living body, an X-ray photographing apparatus, which projects X-rays into a living body from its frontal side and exposes an X-ray film disposed on the rear side of the living body. In the X-ray photograph, its spatial resolution can be improved up to desired value by merely increasing graininess of the film, but there is a limit in improving contrast resolution representing a dynamic range of a gradation because of the developing characteristics ($\gamma$ characteristic) of the film. Therefore, in cases requiring high contrast resolution, such as a diagnosis of lungs, heart or the like, it is almost impossible to make a precise diagnosis when the X-ray photographing apparatus is used.

For this reason, an electronic radiography apparatus has recently been developed in which an X-ray detector is disposed in place of the X-ray film and a radiogram is formed by using an output signal from the X-ray detector. Since this apparatus has components common to those of a computed tomography (CT) scanner, it is frequently assembled into the CT scanner. In the radiography apparatus, the radiogram is formed through electrical processing and is displayed on a monitor such as a CRT, that is, no photographing process is contained in forming the radiogram. Therefore, the contrast resolution of the electronic radiography apparatus is at least 15 to 20 times that of the X-ray photography apparatus. In the apparatus, however, the spatial resolution depends on the number of samples detected, so that a remarkable improvement of it is impossible. More specifically, spatial resolution corresponding to the lateral direction of a human body is determined by the number of cells in the detector which is about 1000 at most. Some portions of the objects under diagnosis partially appear on a picture frequently. In this case, when the radiogram taken is enlarged, the spatial resolution is equivalently improved. In a CT apparatus capable of taking the tomogram, a picture can be enlarged only by shortening the distance between the X-ray source and the living body. In the radiography apparatus in question, the mere shortening of the distance expands only the lateral direction of the human body. Therefore, the lateral and longitudinal expansion rates of the picture are different from each other, with the result that the obtained picture is distorted and can not be used for the diagnosis.

SUMMARY OF THE INVENTION

Accordingly, an object of the present invention is to provide a radiography apparatus which can form a radiogram with a desired expansion rate.

The above object of the present invention is realized by an electronic radiography apparatus comprising a radiation source for projecting a radiation beam in a fan shape in a plane; a radiation detector having a plurality of radiation detecting cells for detecting the radiation beam at a plurality of angular positions within the fan shaped beam; a living body supporting section disposed between the radiation source and the radiation detector, the distance between the living body supporting section and the radiation source being variable; a distance detector for detecting the distance between the living body supporting section and the radiation source; data collecting section for moving the radiation source and the radiation detector together relative to the living body supporting section in a direction orthogonal to the plane in which the radiation beam is radiated in accordance with an output signal from the distance detector, thereby to collect an output signal from the radiation detector; and a circuit for computing an output signal from the data collecting section to form a radiogram of a living body.

DETAILED DESCRIPTION OF THE PREFERRED EMBODIMENTS

Figure 1:
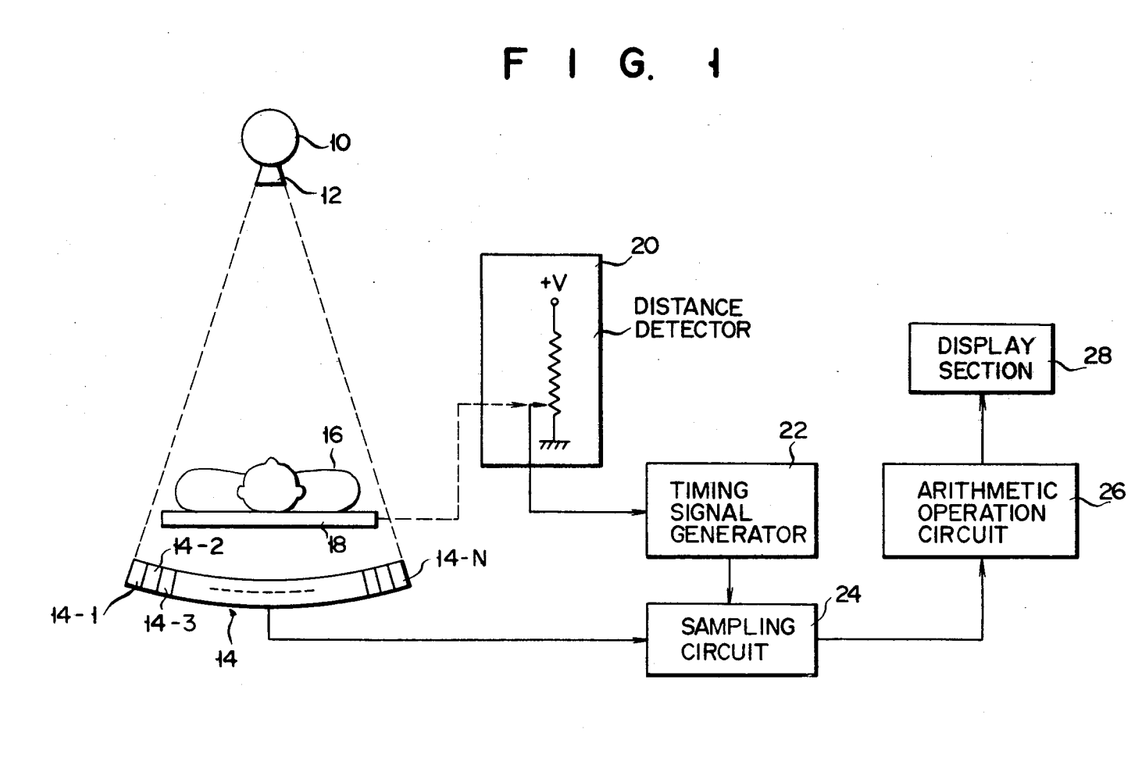
FIG. 1 is a schematic block diagram illustrating an arrangement of an embodiment of a radiography apparatus according to the invention.

An embodiment of a radiography apparatus according to the present invention will be described referring to the accompanying drawings. In FIG. 1, at a radiating portion of an X-ray tube 10, a collimator 12 is provided so that an X-ray beam is projected in a fan or sectoral shape in a plane as indicated by broken lines. The fan shaped radiation X-ray beam is detected at a plurality of angular components of the X-ray beam by an X-ray detector 14 comprised of a number of monosilicon cells or Xe gas cells 14-1, 14-2, ..., 14-N (N=500 to 1000). A table is provided as a support for a living body 16 to be examined. Table 18 is located between the X-ray tube 10 and the X-ray detector 14 orthogonal to the plane of the X-ray beam. Though not shown, a motor is mounted to the table 18 in order to move the table at a constant speed in a direction orthogonal to the plane of the X-ray beam. Upon movement of the table, the relative position of the table 18 to the X-ray beam is changed. Alternatively, the X-ray tube 10 and the X-ray detector 14 are assembled into a unit body and the unit body may be moved at a constant speed along the table 18. The table 18 is also movable in a direction parallel to the plane of the X-ray beam. In other words, the distance between the table 18 and the X-ray tube 10 is variable.

The table 18 is mechanically connected to a movable terminal of a distance detector 20 comprised of a potentiometer connected in series between a +V terminal and a ground terminal. The movable terminal of the potentiometer 20 is moved according to changes of the distance between the table 18 and the X-ray tube 10. The movable terminal of the distance detector 20 is connected to a timing signal generator 22. The timing signal generator 22 produces a timing signal as a pulse signal with a fixed pulse-width repeated at a frequency proportional to the input voltage. The output terminal of the X-ray detector 14 is coupled with the input terminal of a sampling circuit 24 and the output terminal of the timing signal generator 22 is connected to the control terminal of the sampling circuit 24. That is, the sampling circuit 24 operates according to the timing signal produced from the generator 22. The output terminal of the sampling circuit 24 is connected to the input of arithmetic operation circuit 26 which successively stores input signals to execute desired picture processing functions. An output signal of the arithmetic operation circuit 26 is applied to a display section 28.

Figures 2, 3A:
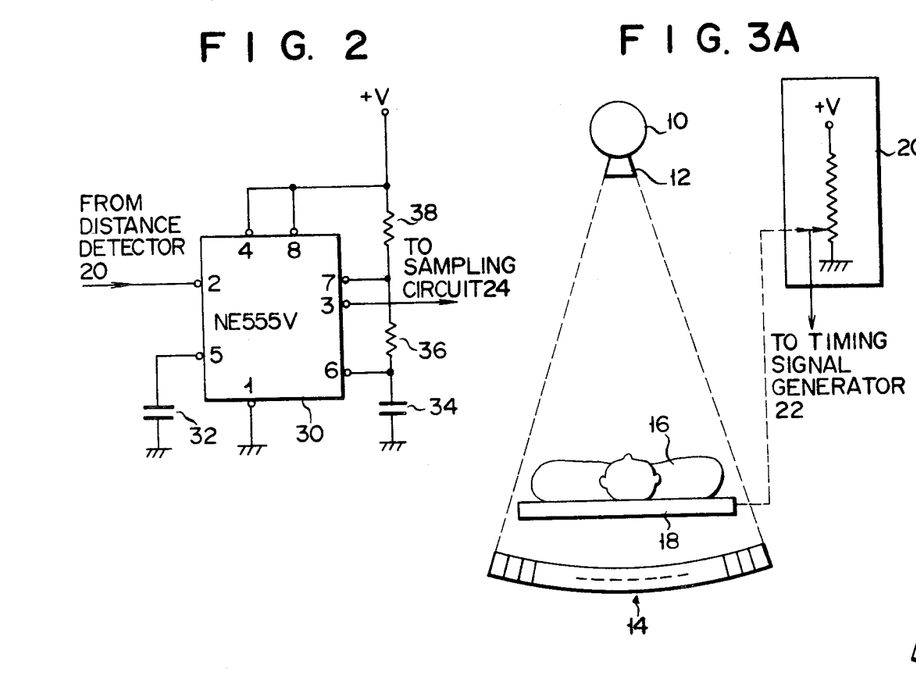
FIG. 2 is a circuit diagram showing an example of a timing signal generator used in the embodiment shown in FIG. 1.
FIGS. 3A and 3B are diagrams useful in explaining positional relations between the living body being examined and the X-ray source.

FIG. 2 is a circuit diagram showing an example of the timing signal generator 22. The generator 22 is a so-called pulse frequency modulation (PFM) circuit using an IC (NE555V) timer circuit 30 manufactured by signetics Inc.. The output terminal of the distance detector 20 is connected to pin 2 of the IC30, and pin 3 is connected with the control terminal of the sampling circuit 24. Pin 1 is grounded; a fifth pin 5 is grounded through a capacitor 32; pin 6 is grounded through a capacitor 34, and also connected to a +V terminal through resistors 36 and 38. Pins 4 and 8 are connected together to the +V terminal, and pin 7 is connected to the junction point of the resistors 36 and 38.

Figure 3B:
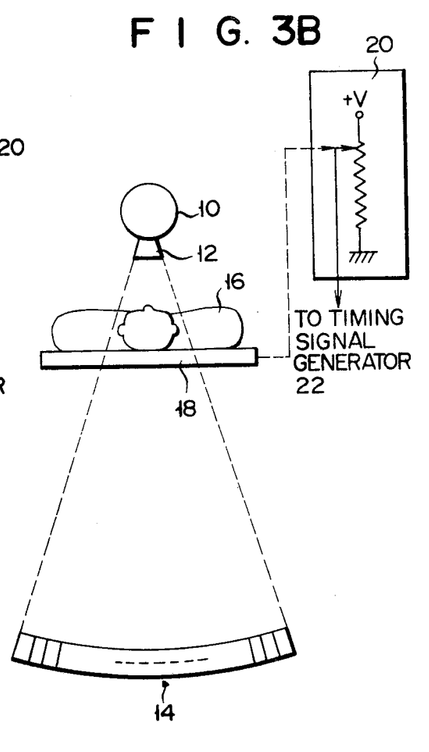

The operation of the above-mentioned embodiment will be described hereafter. The movable terminal of the potentiometer 20 is moved toward ground when the table 18 is far from the X-ray tube 10 as shown in FIG. 3A, while, when the table 18 is near the X-ray tube 10, it is moved toward the +V terminal as shown in FIG. 3B. Accordingly, the distance detector 20 produces a positive voltage signal at a level inversely proportional to the distance between the X-ray tube 10 and the table 18.

As shown in FIG. 3A, where the table 18 is far from the X-ray tube 10, the whole living body 16 lies within the fan shaped area of the X-ray beam, and a radiogram of the whole body under this condition is obtained in the manner described hereafter. For ease of explanation, let an axial direction of the living body 16, i.e. a direction orthogonal to the plane of the drawing be the X direction, the width direction of the living body 16, i.e. the lateral direction on the drawing, is the Y direction, and the direction orthogonal to both the X and Y directions is the Z direction.

For an initial setting, the table 18 is moved so that the X-ray tube 10 is positioned at one end of a diagnosing area of the living body 16 of which a radiogram is desired, as viewed in the X direction. Then, the X-ray beam is radiated in a fan shape through the collimator 12, and the table 18 is moved in the X direction at a constant speed. During the course of the movement of the table 18, the output signals of the detecting cells 14-1, 14-2, . . . , 14-N are sampled given times. Through the samplings, the picture information of picture elements, when the diagnosing area of the living body 16 is divided in matrix fashion, are distributed in the X and Y directions. The number of the samplings is determined by the number of scanning lines of the display section 28. The length of the radiogram in the Y direction is determined by the width of the fan area of the X-ray beam at the position of the living body 16, and the X directional length of the radiogram is determined by the range of movement of the table 18.

Since the display area of the display section 28 is fixed, the X directional length of the radiogram will be determined according to the Y directional length. The X directional length, the distance of movement of the table 18, can be set by changing the sampling period of the output signal from the X-ray detector 14 since the moving speed and the number of the samplings are both constant. For this reason, in this embodiment, the frequency of the timing signal for determining the sampling timing of the sampling circuit 24 is determined by the Z directional length of the radiogram i.e. the distance between the X-ray tube 10 and the table 18.

As the output voltage of the distance detector 20 is low at this time (FIG. 3A), the frequency of the output signal of the timing signal generator 22 is low and the sampling frequency of the sampling circuit 24 is also low. Therefore, the X directional length of the radiogram will cover a long section of the body 16 which is in proportion to the full-width field of view. In this way, after the sampled signal is temporarily stored in the arithmetic operation circuit 26, it is converted into a picture signal according to the scanning in the display section 28. Then, the picture signal is supplied to the display section 28 such as a CRT, where a radiogram is visualized.

The operation of the photography apparatus when the table 18 is made to approach to the X-ray tube 10, as shown in FIG. 3B, will now be described. Assume now that the distance between the X-ray tube 10 and the table 18 is half that in the case of FIG. 3A. In this case, the X-ray beam is assumed to cover a part (less than full width) of the living body 16, for example, the lungs alone, as shown in FIG. 3B. Accordingly, the radiogram of the lungs alone is displayed by the display section 28 and the size of the lungs is larger than that in the radiogram of FIG. 3A. That is, the field of view depicted in FIG. 3B is reduced and the image will appear to be magnified relative to the image produced in the FIG. 3A condition. The Y directional (width) expansion factor is inversely proportional to the distance between the X-ray tube 10 and the table 18.

Therefore, in order to make the expansion in the X direction equal to that in the Y direction, i.e., to increase the X directional expansion, all one has to do is to shorten the sampling period and the moving distance of the table 18. In this example, the interval between the X-ray tube 10 and the table 18 is ½ that of the FIG. 3A case. Therefore, the Y directional expansion of the radiogram is doubled. The level of the output voltage from the distance detector 20 varies in accordance with the distance between the X-ray tube 10 and table 18 with the FIG. 3A arrangement as a reference. Therefore, the frequency of the output signal from the timing signal generator 22 is doubled, while the sampling frequency of the sampling circuit 24 is halved. As a result, the moving distance of the table 18 is shortened to be ½ and the X directional expansion factor (apparent image magnification) of the radiogram is doubled.

As described above, according to the present embodiment, the expansion of the radiogram in the axial direction of the living body can be enlarged by sampling the output signal from the X-ray detector at a period corresponding to the Y directional expansion factor during the course of moving the table at a fixed speed when the expansion of the radiogram in the Y direction of the living body is increased by making the living body close to the X-ray tube. Therefore, a radiogram with a desired expansion factor can be obtained and a radiography apparatus with a high spatial resolution can be realized. Since the radiography apparatus has essentially a high contrast resolution, a detailed diagnosis of the living body is possible precisely. Further, since the radiogram information is temporarily stored in the arithmetic operation circuit, picture processing suitable for the diagnosis can easily be realized.

Figure 4:
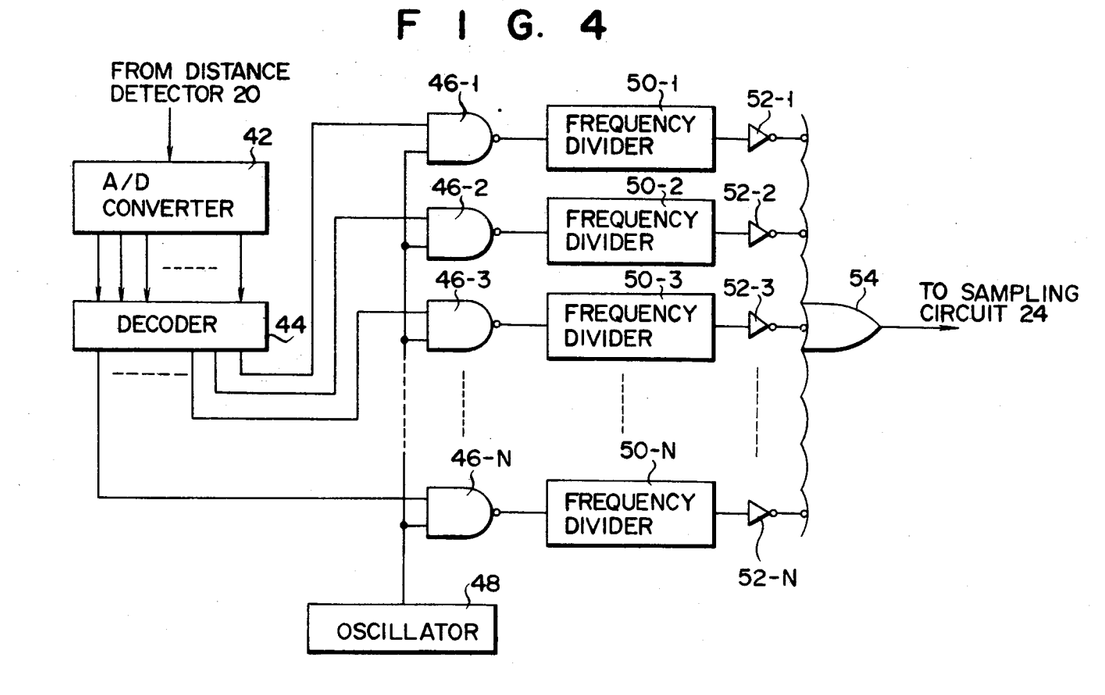
FIG. 4 is a circuit diagram showing another example of the timing signal generator.

While the X-ray is used for the radiation in the above-mentioned embodiment, γ-ray may be used for the same purpose. In this case, a γ-ray source and a γ-ray detector are used in place of the X-ray tube and the X-ray detector. In the above-mentioned embodiment, the PFM circuit utilizing the IC for timer is used for the timing signal generator 22 for determining the sampling frequency of the sampling circuit. This type PFM circuit may be substituted by a PFM circuit comprised of indinidual components as shown in 4, described hereinafter. The output signal from the distance detector 20 is supplied to a decoder 44 through an A/D converter 42. The decoder 44 is provided with a plurality of output terminals which are each connected to one input terminal of NAND gates 46-1, 46-2, . . . , 46-N, respectively. An output signal from an oscillator 48 is coupled with the other input terminal of the NAND gates 46-1, 46-2, . . . , 46-N. Output signals from the NAND gates 46-1, 46-2, . . . , 46-N are respectively supplied to frequency dividers 50-1, 50-2, . . . , 50-N whose frequency-dividing ratios are different each other. Output signals from the frequency-dividers 50-1, 50-2, . . . , 50-N are supplied to a NOR gate 54, through respective inverters 52-1, 52-2, . . . , 52-N. An output terminal of the NOR gate 54 is connected to the control terminal of the sampling circuit 24.

The operation of the PFM circuit shown in FIG. 4 is as follows. An output analog value from the distance detector 20 is converted into a corresponding digital signal by the A/D converter 42 and is supplied to the decoder 44. The decoder 44 produces a signal at a logic high level (referred to as an H level) to only one output terminal selected in accordance with an input value. As a result, only the NAND gate connected to that output terminal at the H level conducts, while the remaining NAND gates are always at the H level at the output terminals and are nonconductive. Accordingly, the output pulse signal from the oscillator 48 is supplied through the NAND gate to the frequency divider of which the output signal in turn is supplied through the inverter and the NOR gate to the sampling circuit 24. Here, the selected frequency divider is determined in accordance with the output signal from the decoder 44, i.e., the output signal from the distance detector 20. In this way, the timing pulses at a frequency corresponding to a level of the output signal from the distance detector 20 are supplied to the sampling circuit 24.

In FIG. 4, the circuitry in which the decoder may be replaced by one which responds to the input data to produce numerical data. Then, a preset value of a presetable counter is set by the output data from the decoder and an output signal from the oscillator is frequency-divided at a given ratio by the presetable counter. The PFM circuit may be substituted by a V/F converter such as a voltage controlled oscillator.

Since the many components constituting the embodiment are the same as those in the CT scanner, the radiography apparatus may be incorporated into the CT scanner system. In the CT scanner, the living body is radiated with the X-rays and the output signal from the detector is arithmatically processed, while the X-ray source and the detector are moved together relative to the living body in the axial direction of the living body. With such a system the radiography apparatus of the invention can be operated to facilitate precise location of the slicing position of the living body for which a tomogram is desired.

Additionally, the distance between the X-ray tube 10 and the table 18 may be detected by measuring the propagation time of ultrasonic wave energy, without using the potentiometer. An ultrasonic generating source and ultrasonic detector are mounted at a location of the table 18 not in contact with the living body 16. The distance is detected by using the propagating time of the ultrasonic wave when the ultrasonic wave produced from the ultrasonic wave generating source and reflected from the X-ray tube 10 is detected by the detector.

A second embodiment of a radiography apparatus according to the invention will next be described. Like parts in the second embodiment are designated by like reference numerals in the first embodiment and the explanation thereof will be omitted. In the second embodiment shown in FIG. 5, the essential difference from the first embodiment are that an output signal of the timing signal generator 22 is applied to a control terminal of a controllable power supply 62, as well as to the input of sampling circit 24. The output of the controllable power supply 62 is coupled with an input terminal of a high voltage generator 64 comprised of a transformer and a rectifier, and the output of generator 64 is supplied to the X-ray tube 10.

Figure 5:
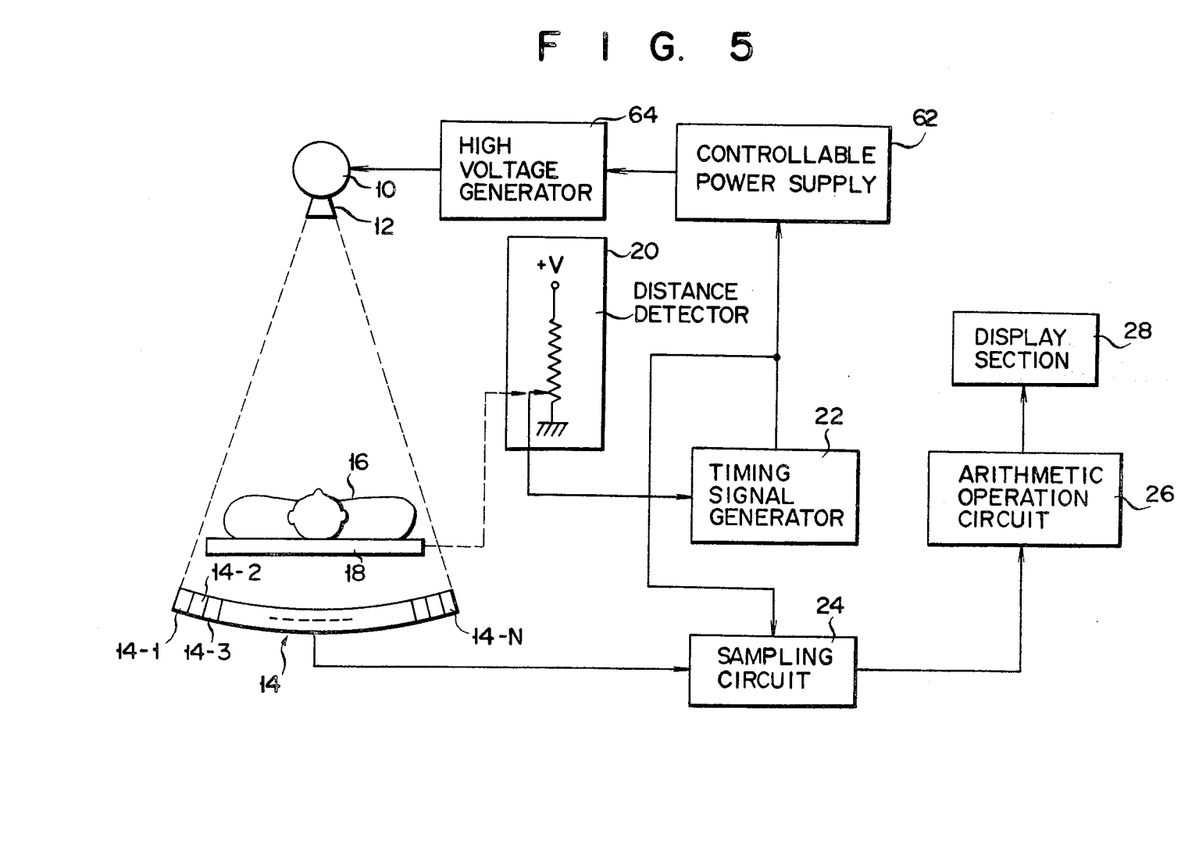
FIG. 5 is a schematic block diagram of a second embodiment of a radiography apparatus according to the invention.

In the operation of the second embodiment, as in the first embodiment, the sampling frequency of the X-ray detector 14 changes in accordance with the change of the distance between the table 18 and the X-ray tube 10. Accordingly, a radiogram with a desired expansion (enlargement) factor is obtained. Further, in the second embodiment, the controllable power supply 62 applies a voltage to the high voltage generator 64 in response to the output signal of the timing signal generator 22. Therefore, X-ray energy tube 10 radiates the X-ray beam intermittently only when the sampling circuit 24 samples the output signal of the X-ray detector 14. Therefore, the dosage of X-rays imposed on the living body is remarkably reduced since radiation is emitted only when collection of the radiogram information is necessary. Further, since the X-rays are intermittently radiated, accuracy of the sampling of data is improved, and hence spatial resolution of the radiogram is also improved.

As a switching element of the controllable power source 62, a semiconductor switching element such as a thyristor or an electromagnetic switch, may be used. While in this embodiment the generation of a high voltage is controlled on the primary side of the high voltage generator 64, it may be controlled on the secondary side by using a tetrode switch, etc.

Figure 6:
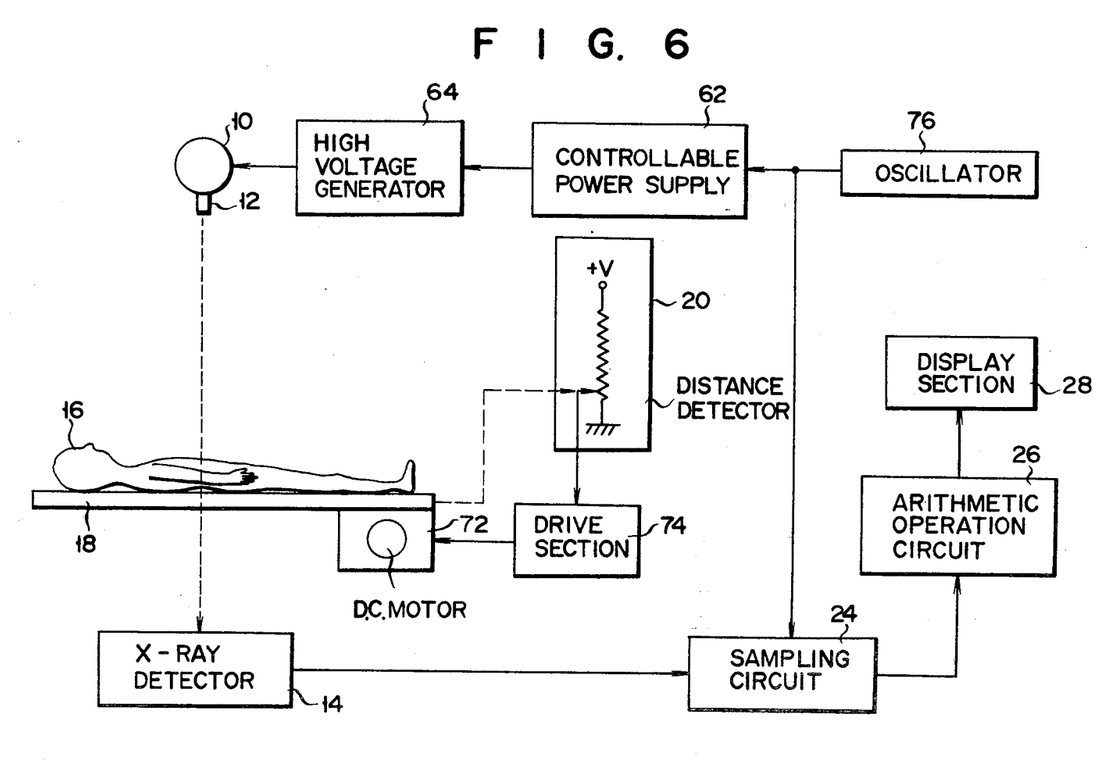
FIG. 6 is a schematic block diagram of a third embodiment of radiography apparatus according to the invention.

FIG. 6 shows a third embodiment of radiography apparatus according to the invention. In FIG. 6, which illustrates the living body 16 and the table 18 is viewed in a lateral direction, the lateral direction (axis of body 16) is the X direction and the direction orthogonal to the plane of the drawing is the Y direction (width direction of FIG. 1). A DC motor 72 is mounted to the table 18, and the X directional moving speed of the table 18 is changeable by the DC motor 72. The distance between the table 18 and the X-ray tube 10 can be changed as in the first and second embodiments. The output signal of the distance detector 20 corresponding to the position of the table 18 in the Z direction, i.e., the distance between the table 18 and the X-ray tube 10, is applied to a drive section 74, and the output signal of the drive section 74 is supplied to the DC motor 72. The speed of motor 72 is proportional to the output from distance detector 20. Since the potentiometer is connected so that the output signal is highest when Δ Z is greatest, the motor 72 will decrease in speed as table 18 is moved toward X-ray tube 10. The output signal of an oscillator 76, which produces a pulse signal with a fixed frequency, is supplied to the control terminal of the controllable power source 62 and the control terminal of the sampling circuit 24.

Figure 7:
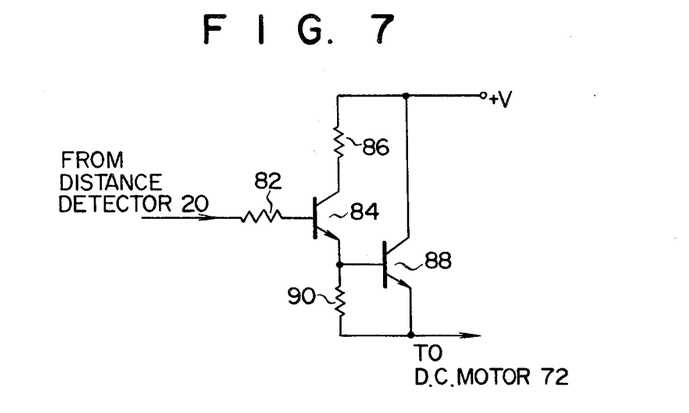
FIG. 7 is a circuit diagram showing an example of drive circuit of the embodiment shown in FIG. 6.

The drive section 74 is a current amplifier arranged as shown in FIG. 7. The output signal of the distance detector 20 is applied to the base of an NPN transistor 84 through a resistor 82. The collector of the transistor 84 is connected to a +V power source terminal through a resistor 86. The emitter of the NPN transistor 84 is directly connected to the base of NPN transistor 88, and is further connected to the emitter of the transistor 88 through a resistor 90. The collector of the transistor 88 is connected with the +V power source terminal and its emitter is coupled with the DC motor 72.

The operation of the third embodiment will be described. The X-ray tube 10 radiates X-ray beams intermittently at a fixed frequency in response to the output pulse signal from the oscillator 76. The sampling circuit 24 samples the output signal of the X-ray detector 14 in synchronism with the radiation of the X-ray beam in response to the output pulse signal from the oscillator 76. In this example, as shown in FIG. 3B, when the distance between the table 18 and the X-ray tube 10 becomes short and the Y directional enlargement of the radiogram is large, it is necessary to shorten the X directional moving distance of the table 18 and to decrease the X directional sampling increment. As the number of samplings is fixed, the X directional moving distance of the table 18 is made short by decreasing the moving speed of the table. In this embodiment, when the distance between the table 18 and the X-ray tube 10 becomes short, the output voltage of the distance detector 20 goes low. As a result, the signal level applied to the DC motor 72 goes low. Accordingly, the rotating speed of the DC motor 72 is reduced and the X directional moving speed of the table 18 decreases. Then, the distance which the table 18 moves when the output signal of the X-ray detector 14 is sampled a given number of times at a fixed period, becomes short. Thus, according to the embodiment, it is possible to enlarge the radiogram at will be changing the moving speed of the living body.

Figure 8:
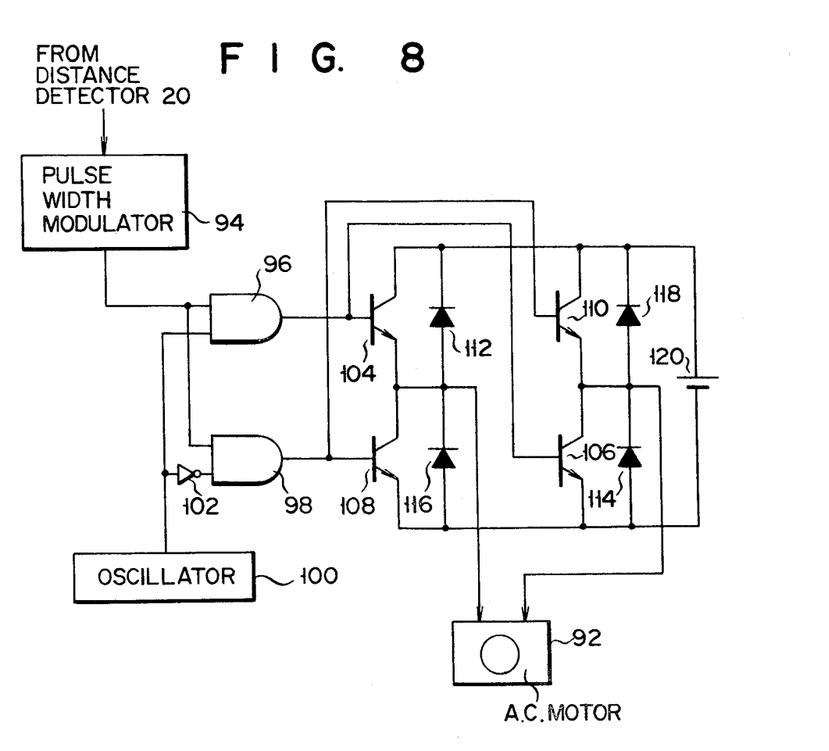
FIG. 8 is a circuit diagram illustrating another example of the drive circuit.

Another modification of the drive section for controlling the moving speed of the table 18 in response to the output signal of the distance detector 20 will next be described referring to FIG. 8. In this modification, an AC motor 92 is used instead of the DC motor 72. The output signal of the distance detector 20 is applied to input terminals of AND gates 96 and 98 through a pulse width modulator 94. The output terminal of an oscillator 100 is connected to the other input terminal of the AND gate 96 and an input terminal of an inverter 102, and an output terminal of the inverter 102 is coupled with the other input terminal of the AND gate 98. The output terminal of the AND gate 96 is connected to bases of transistors 104, 106. The output terminal of AND gate 98 is connected to the bases of transistor 108, and 110. The transistors 104, 106, 108 and 110 are bridge-connected. The transistors 104, 106, 108 and 110 are connected with diodes 112, 114, 116 and 118 in parallel, respectively, forming a bridge inverter. The series circuit of transistors 104 and 108 is connected in parallel with a power source 120. Another series circuit of the transistors 104 and 110 is connected in parallel with the AC motor 92.

In the operation of the drive section, a pulse signal with a pulse width corresponding to a level of the output signal from the distance detector 20 is alternately applied from the pulse width modulator 94 to the AND gates 96 and 98 in response to the output pulse of the oscillator 100. The AND gates 96 and 98 drive a pair of the transistors 104 and 106 and another pair of the transistors 108 and 110 in the vision of inverters. The AC motor 92 is rotated in response to collector currents of the transistors 106 and 108. Since the collector currents depend on the pulse width of the output pulse from the PWM circuit 94, the AC motor 92 is rotated at a power corresponding to the distance between the table 18 and the X-ray tube 10.

The modification as described in the first embodiment is applicable for the second and the third embodiments. For example, the X-ray may be substituted by a γ-ray. the radiation source 10 and the detector 14 may be moved together, instead of the table 18. Further, these modifications may be incorporated into a CT scanner. As described above, radiography apparatus for obtaining a radiogram with a desirable expansion factor is provided according to the invention. It is evident that this invention is not limited to the above-mentioned embodiments, and may be variously changed or modified within a scope of the invention.

What is claimed is:

1. A radiography apparatus comprising:
   radiation means for transmitting a fan-shaped beam of radiation in a plane;
   detector means for detecting said transmitted radiation at a plurality of spaced points in said plane and for producing data output signals in response to detected radiation;
   support means for positioning an object between said radiation means and said detector means whereby said object is irradiated for examination by said beam of radiation;
   positioning means for moving said support means toward and away from said radiation means and including means for generating a distance signal indicating the distance of said support means from said radiation means;
   drive means for moving said support means in a direction substantially orthogonal to the plane of said fan-shaped radiation beam;
   data collecting means for collecting said data output signals at timed sampling intervals as said object is moved by said drive means through the plane of said beam;
   sampling control means receiving said distance signal and being responsive thereto to control the sampling of said data output signals by said data collecting means so that the distance moved by said object between consecutive sampling intervals is controlled as a direct function of the distance between said radiation means and said support means; and means for forming a radiogram from data output signals collected by said data collecting means.

2. The radiography apparatus of claim 1 in which said drive means moves said support means at a constant velocity and in which said sampling control means controls the frequency of occurrence of said timed sampling intervals so that said frequency is inversely proportional to the distance between said radiation means and said support means.

3. The radiography apparatus of claim 1 in which said data collecting means collects said data output signals at timed sampling intervals which occur at a constant repetition rate and in which said sampling control means controls the velocity at which said drive means moves said support means so that said velocity is directly proportional to the distance between said radiation means and said support means.

4. A radiography apparatus according to claim 1 wherein said radiation means includes an X-ray tube and collimator mounted adjacent to a radiating section of said X-ray tube for reforming the radiated X-ray into a fan shape in said plane, and wherein said radiation detecting means comprises a plurality of monosilicon cells.

5. A radiography apparatus according to claim 1 wherein said radiation means includes an X-ray tube and collimator mounted adjacent to a radiating section of said X-ray tube for reforming the radiated X-ray into a fan shape in said plane, and wherein said radiation detecting means comprises a plurality of Xe gas cells.

6. A radiography apparatus according to claim 1 wherein said means for generating said distance signal includes a potentiometer having a movable terminal arranged to move with said support means.

7. A radiography apparatus according to claim 1 in which said data collecting means includes an oscillator for producing a first pulse signal at a fixed frequency and a sampling circuit for sampling said data output signals at a fixed frequency in response to said first pulse signal, and in which said sampling control means includes a drive section for controlling said drive means to move said support means at a velocity according to the level of said distance signal.

8. A radiography apparatus according to claim 1 in which said means for forming said radiogram includes an arithmetic circuit for performing image processing by successively storing data output signals from said data collecting means and for producing image output signals, and a display section for displaying an image in accordance with said image output signals.

9. A radiography apparatus according to claim 7 in which said drive section includes a pulse width modulator for producing a second pulse signal having a pulse width substantially proportional to the level of said distance signal, a switch circuit with first and second output terminals for presenting said second pulse signal at first and second output terminals, a bridge inverter circuit in which said two output signals from said switch circuit are respectively applied to pairs of transistors, each of said pairs constituting opposite sides of said bridge inverter, and in which said drive means comprises an alternating current motor connected as a load to said bridge inverter circuit and constructed and arranged to drive said support means.

10. A radiography apparatus according to claim 7 in which said drive section includes an amplifier for amplifying said distance signal and a direct current motor rotated under control of said drive section at a speed substantially proportional to the level of said amplified distance signal.

11. A radiography apparatus according to claim 1 in which said sampling control means includes a timing signal generator for producing a pulse signal output having a fixed pulse width and a frequency determined by the level of said distance signal, in which said data collecting means includes a sampling circuit for sampling said data output signals at timed intervals controlled by said pulse signal output from said timing signal generator, and in which said drive means moves said support means at a fixed velocity in said orthogonal direction.

12. A radiography apparatus according to claim 11 in which said radiation means intermittently transmits said beam during intervals synchronized with said pulse signal output from said timing signal generator.

13. A radiography apparatus according to claim 11 or 12 in which said timing signal generator includes a pulse frequency modulator.

14. A radiography apparatus according to claim 11 or 12 in which said timing signal generator includes an analog to digital converter for converting said distance signal into a digital signal, an oscillator for producing an intermediate pulse signal at a fixed frequency, and a frequency divider for frequency-dividing said intermediate pulse signal in accordance with said digital signal to produce said pulse signal output.

* * * * *